(12) United States Patent
Provost

(10) Patent No.: US 6,491,390 B1
(45) Date of Patent: Dec. 10, 2002

(54) CLIP-ON GLASSES

(76) Inventor: Jack Provost, 17F Canterbury Rd., Chatham, NJ (US) 07928

( * ) Notice: Subject to any disclaimer, the term of this patent is extended or adjusted under 35 U.S.C. 154(b) by 0 days.

(21) Appl. No.: 09/956,638

(22) Filed: Sep. 21, 2001

(51) Int. Cl.[7] .................................................. G02C 3/00
(52) U.S. Cl. ............................................ 351/155; 2/10
(58) Field of Search ........................... 351/41, 44, 155, 351/158; 2/10, 453

(56) References Cited

U.S. PATENT DOCUMENTS

| | | | |
|---|---|---|---|
| 700,587 A | 5/1902 | Waldron | 351/41 |
| 1,228,341 A | 5/1917 | Maynard | 351/41 |
| 1,514,111 A | 11/1924 | Sutton | 351/41 |
| 1,665,513 A | 4/1928 | Thomas | 351/41 |
| 1,833,741 A | * 11/1931 | Diehl | 351/155 |
| 1,955,232 A | 4/1934 | Gallaway | 2/10 |
| 2,519,959 A | 8/1950 | Fisher | 2/10 |
| 2,560,669 A | 7/1951 | Vaca | 2/10 |
| 2,691,164 A | 10/1954 | Feldman | 2/10 |
| D220,290 S | 3/1971 | Bloch | D16/8 |
| 4,304,005 A | 12/1981 | Danley, Sr. | 2/10 |
| 4,541,125 A | 9/1985 | Phillips | 2/10 |
| D293,450 S | 12/1987 | Jannard | D16/102 |
| 4,810,080 A | 3/1989 | Grendol | 351/41 |
| 4,819,274 A | 4/1989 | Day | 2/10 |
| 4,859,048 A | 8/1989 | Jannard | 351/159 |
| 4,951,316 A | * 8/1990 | Moody | 351/155 |
| 5,007,109 A | 4/1991 | Wheeler | 2/10 |
| D322,081 S | 12/1991 | Longsdorf | D16/102 |
| 5,129,102 A | 7/1992 | Solo | 2/10 |
| D329,445 S | 9/1992 | Jannard | D16/102 |
| 5,208,916 A | 5/1993 | Kelman | 2/10 |
| 5,261,124 A | 11/1993 | Day | 2/10 |
| 5,412,812 A | 5/1995 | Gatchalian | 2/10 |
| 5,422,686 A | 6/1995 | Kelman et al. | 351/155 |
| D367,873 S | 3/1996 | Connolly et al. | D16/304 |
| 5,687,420 A | * 11/1997 | Chong | 2/10 |
| 5,696,571 A | 12/1997 | Spencer et al. | 351/47 |
| 6,031,169 A | 2/2000 | Coppola | 84/411 |
| 6,246,323 B1 | 6/2001 | Fischbach | 340/539 |

* cited by examiner

Primary Examiner—Huy Mai
(74) Attorney, Agent, or Firm—Thomas L. Adams

(57) ABSTRACT

An assembly for attachment to the bill of a cap comprises a curved lens panel, and a pivot member to receive the lens and attach it to a frame. The pivot member includes a lens retaining member formed by a curvilinear wall that extends from the body, and the body's curved ends form receptacles that receive the lens panel's ends; the lens panel can be readily inserted and removed, enabling the user to interchange lenses, using different styles, colors, or prescriptions. The pivot member includes a hinge enabling the lens to be pivoted into several positions, and a middle member connecting the lens retaining receptacle with the hinge. The frame has curved ends which form a gripper opening for receiving the bill of a cap, and a barb which engages the bill. Screws threaded through the frame ends also aid in attaching the eyeglass assembly to the bill.

19 Claims, 3 Drawing Sheets

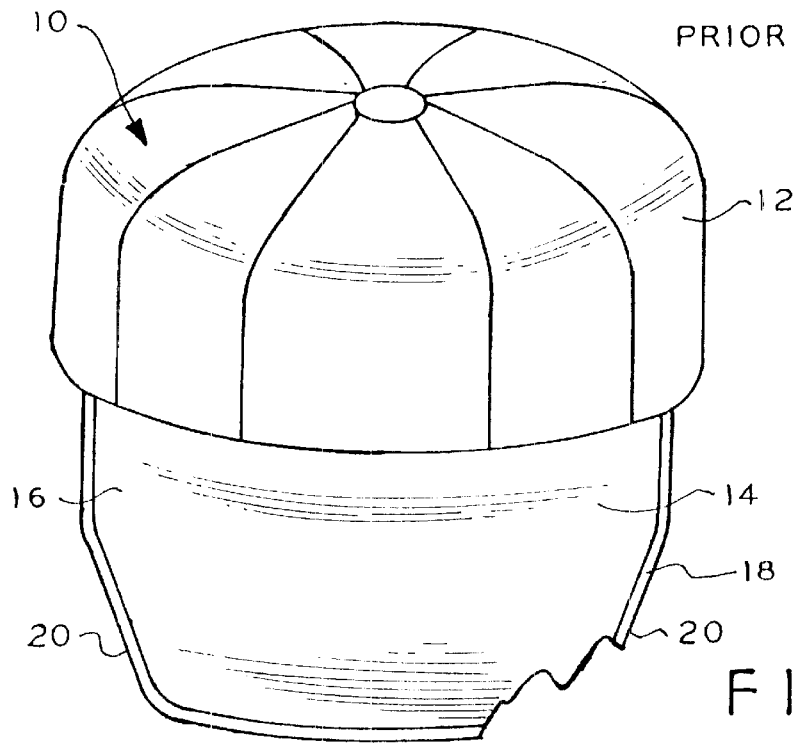
FIG. 1
PRIOR ART
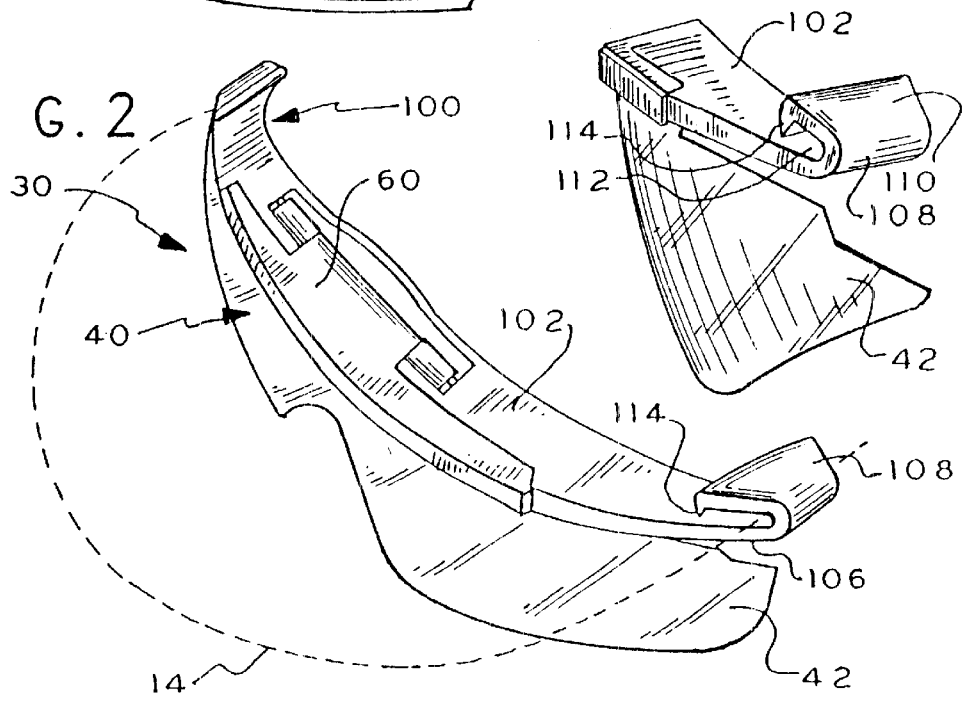
FIG. 2
FIG. 3

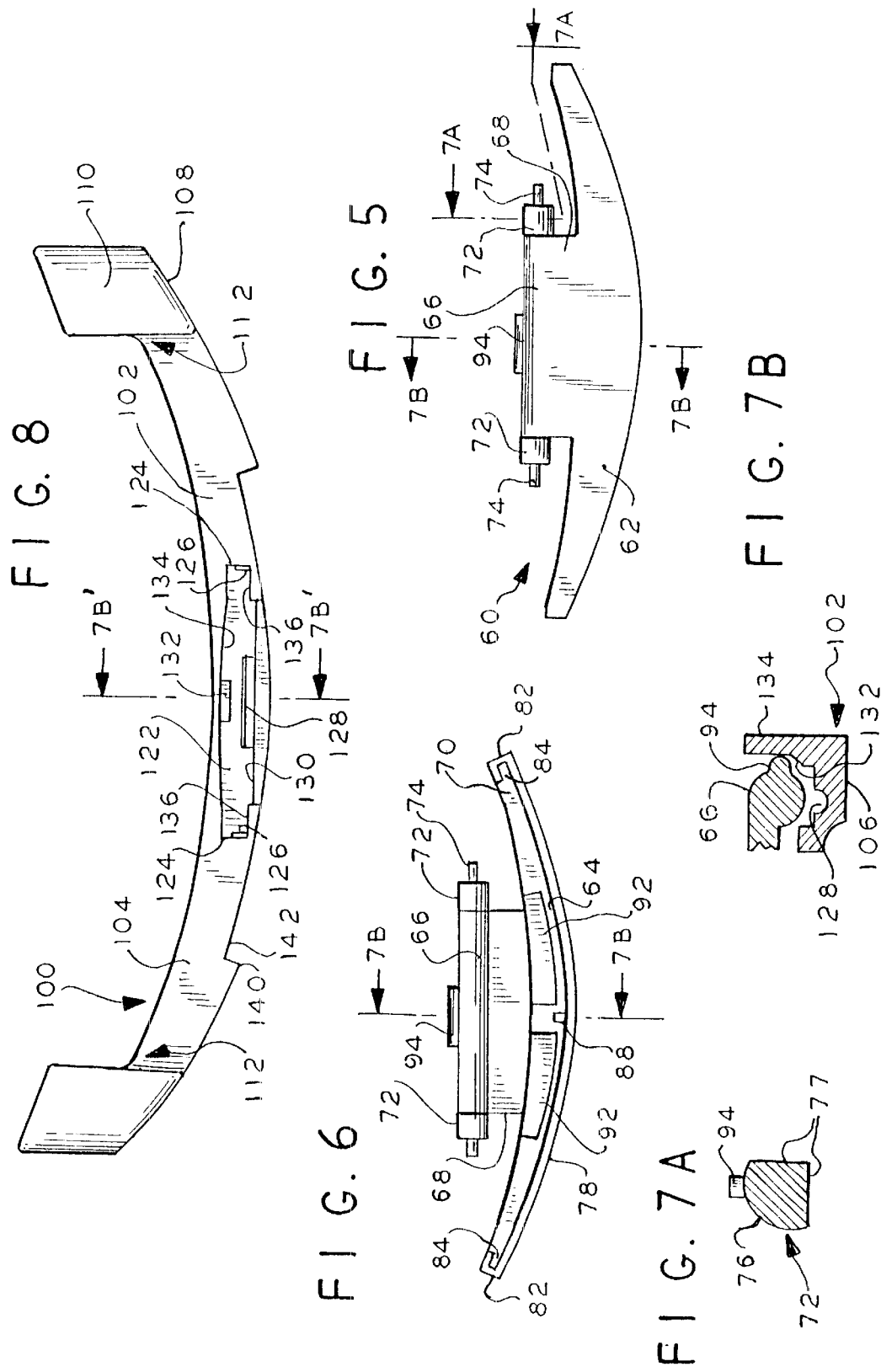

CLIP-ON GLASSES

BACKGROUND OF THE INVENTION

1. Field of the Invention

The present invention relates to sunglasses (and other eyeglasses), which are attached to the bill or visor of a cap. In particular, the present invention relates to attachable sunglasses in which the lens can be moved into one of several positions.

2. Description of Related Art

Sunglasses or other eyeglasses that are attachable to a hat are known in the prior art. In U.S. Pat. No. 5,422,686 Kelman et al. disclose an eyeglass assembly for visored headgear which includes an adjustable clip for attaching the eyeglasses to the visor. The distance between the clips is adjustable, enabling the user to vary the distance between the eyeglasses and the user's eyes. The attachment of the eyeglasses to the visor is relatively insecure. Also, the lens is fixed to posts on a hinge and is therefore not easily replaced.

In U.S. Pat. No. 5,129,102 a base having a pair of C-shaped clips is attached by VELCRO™ tape to the underside of the bill of a cap. A pair of ordinary sunglasses has cylindrical members that snap into the C-shaped clips to rotatably support the sunglasses. In another embodiment, the C-shaped clip is placed on the sunglasses themselves. The lens cannot be readily replaced without disassembling the hinge.

U.S. Pat. No. 4,304,005 discloses a pair of wire frames secured by VELCRO™ straps to the bill of a cap. A flat shield is pivotally mounted to the two wire frames to flip either in front of the wearer's face or up under the bill. The shield is slidably held in four small clips lacking any securing means. Being slidable, the position of the shield relative to the hinge is highly variable. Also, while the shield is replaceable, its slidability leaves it prone to falling out of the clips. In the up position the shield apparently extends past the outer end of the bill.

U.S. Pat. No. 4,541,125 discloses a relatively long band having a pair of flat hooks that clip onto the bill of a cap. The center of the band has a bar which supports a C-shaped clip providing a hinge for a set of rotatable eyeglasses. The lens could not be readily replaced without disassembling this hinge. The eyeglasses curve to conform to the inner curved surface of a conventional cap visor. The eyeglasses have a projection that spaces the eyeglasses from the point of rotation. The glasses are mounted on the visor by means of a rigid clip having a hooked end portion into which the visor is received.

In U.S. Pat. No. 2,560,669 a T-shaped structure is riveted to the underside of a cap bill. A sheet of sunglass material is riveted to a hinge plate that is hinged to the structure riveted onto the bill. Thus the sunglass material cannot be readily replaced without disassembling the hinge. The hinge has an over center spring to snap the sunglasses into position. The sunglass material has a wrap around feature.

In U.S. Pat. No. 1,228,341 eye shield material is secured by indentations in a holder that is an integral part of a hinge. The holder is hinged to a pair of fingers that clip onto the tip of the bill of a cap. Interchangeable eye shields are not disclosed. Even if one attempted to defeat the indentations and replace the eye shield, there is no mechanism to properly position the shield relative to the hinge.

U.S. Pat. No. 1,514,111 discloses a wire band encircling the bill of a cap, with an eyeglass frame rotatably mounted to the wire beneath the bill. A pair of monocular eye pieces are each suspended from a wire inserted through a hole in the eye piece frame. This form of suspension is unstable and will leave the eye pieces with a tendency to swing about the hole. See also U.S. Pat. No. 5,412,812 for another single point attachment with a narrow clip U.S. Pat. Nos. 2,519,959 and 2,691,164 both show a pair of clips supporting a ball to provide a ball joint connection to eye shields. Arms riveted to the eye shields form part of the ball joint. Thus, the eye shields cannot be readily replaced without disassembling the ball joint.

U.S. Pat. No. 700,857 discloses a plate having key hole-shaped notches which are used to hold lenses either up against the underside of a bill or in front of a wearer's face. The lenses cannot be readily replaced without disconnecting the assembly at the key hole-shaped notches.

In U.S. Pat. No. 4,819,274 a lens is frictionally mounted in a U-shaped channel that has an integral hinge pin. This reference mentions removing the lens. Regardless, the U-shaped channel lacks any means for centering the lenses with respect to the hinges. See also U.S. Pat. No. 5,208,916.

For non-flip-up eye shields that attach to the bill of a cap or the brim of a hat, see U.S. Pat. Nos. 1,665,513; 1,955,232 and 5,007,109.

See also U.S. Pat. Nos. 4,810,080; 4,859,048; and 5,261,124; as well as Design Pat. Nos. 220,290; 293,450; 322,081; and 329,445.

Thus, there is a need for a sunglass or eyeglass assembly which can be easily attached to and be retained on a cap, and in which the lens can be easily removed, either for replacing damaged lenses, changing styles or colors, or use of different prescription lenses, as can be achieved with the present invention.

SUMMARY OF THE INVENTION

It is an object of the present invention to provide a pair of sunglasses or other eyeglasses that can be attached to the bill of a cap.

Another object of the present invention is to provide a pair of glasses whose position can be adjusted upwards or downwards.

Another object of the present invention is to provide sunglasses whose lenses are removable and which can be replaced with lenses having different colors, styles, or in the case of prescription glasses, with a lens having a different prescription.

Still another object of the present invention is to provide a pair of sunglasses which can be attached above and below the bill of a cap using a combination of a fastener and a barb.

Still another object of the present invention is to provide sunglasses that can be economically manufactured from durable materials.

Another object of the present invention is to provide a cap having removable tilt-up sunglasses, which is economical to manufacture, and which can be easily used by the wearer to tilt the glasses up and down.

Another object of the present invention is to provide a combination cap with an attached pair of tilt-up sunglasses.

In accordance with the illustrative embodiments demonstrating features and advantages of the present invention, there is provided a glasses assembly for attachment to the bill of a cap. The eyeglass assembly includes a frame, a pivot member, and a set of lens members having different characteristics. The pivot member has a lens retaining receptacle for releasably holding any one of the lens member. The lens members are interchangeable in the pivot member. The lens retaining receptacle is arranged to restrict placement of the lens members to a predetermined centered position. The pivot member includes: (i) a body having a base and a wall depending from the base, and (ii) a hinge having at least one pivot pin and at least one detent feature for holding the pivot member in one or more predetermined positions. The frame terminating in a pair of ends each having a curved upper portion, the ends including a gripper opening for gripping the bill of a cap.

In accordance with another aspect of the invention an eyeglass assembly is provided for attachment to the bill of a cap. The eyeglass assembly has a lens member comprising a lens panel having an upper portion with an alignment notch therein. The upper portion includes a pair of ends. Also included is a pivot member comprising a body and a hinge. The body including a base, and a curvilinear wall depending from the base. The curvilinear wall has an alignment pin connected thereto. The curvilinear wall terminates in a pair of curved ends, thereby forming a lens retaining member. The curved ends further comprise a receptacle therein for receiving the lens member. The hinge is connected to the body and includes a detent ridge. The lens members are removable and interchangeable from the pivot member to accommodate alternate styles or colors. The eyeglass assembly includes a frame comprising an arcuate body terminating in a pair of ends. These ends have a curved upper portion terminating in a barb. These ends also include a gripper opening therein into which gripper opening the bill of a cap is receivable with the barb gripping the bill. The ends of the frame have a threaded opening in a lower portion of the body end. Each of the threaded openings receive a fastener therethrough. The bill is received within the gripper opening. The fastener engages the bill when the fastener is urged into engagement with the bill.

In accordance with yet another aspect of the invention there is provided, in combination, an eyeglass assembly attached to the bill of a cap. The eyeglass assembly includes a frame, a pivot member, and a lens member comprising a lens panel having an upper portion with an alignment notch therein. The pivot member comprises a body including a base, and a curvilinear wall depending from the base. The curvilinear wall has an alignment pin connected thereto. The curvilinear wall terminates in a pair of curved ends, thereby forming a lens retaining member. The curved ends further comprise a receptacle therein for receiving the lens member. The pivot member also includes a hinge having a detent ridge and terminating in a pair of pins. The pivot member also has a middle member connecting the lens retaining member with the hinge. The lens members are removable from the pivot member and lens members of alternate styles or colors are interchangeable. The frame comprises an arcuate body terminating in a pair of ends. These ends have a curved upper portion, terminating in a barb. These ends also include a gripper opening therein receiving the bill of the cap, the barb gripping the bill. A threaded opening is formed in a lower portion of the body end. Each threaded opening receives a fastener therethrough. The fastener is in threaded engagement with the bill.

By employing structure of the foregoing type, an improved eyeglass assembly is achieved. A preferred sunglass assembly is designed to fit under the bill of a cap next to the wearer's forehead. The sunglasses are mounted on a frame to space them from the underside of the bill. The pivot point of the sunglasses is spaced from the bill. The sunglasses can flip down so they are in front of the wearer's face or can be stored up against the underside of the bill. Preferably, the sunglasses have a relatively large lens panel that curves on its ends to shield the eyes from side glare and also has a notch for the wearer's nose.

The preferred method of mounting the sunglasses is by hooked grippers with screws for securing the assembly to the bill. A barb, also present on the frame, engages the upper surface of the bill while the screws attach the sunglasses to the bottom surface of the bill.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein:

FIG. 1 is a plan view of a typical baseball-style cap;

FIG. 2 is a perspective view of the bill clip-on, tilt-up sunglasses according to principles of the present invention;

FIG. 3 is a detailed side view of the end, prong and gripper opening of frame body of FIG. 2;

FIG. 5 is a top plan view of the pivot member of FIG. 1;

FIG. 6 is a bottom plan view of the pivot member of FIG. 5;

FIG. 7A is a sectional view of the hinge, taken along line 7A—7A of FIG. 5;

FIG. 7B is a sectional view of the hinge, taken along line 7B—7B of FIG. 5 and superimposed on the associated portion of the frame, as taken along line 7B'—7B' of FIG. 8;

FIG. 8 is a top plan view of the frame of FIG. 1; and

DETAILED DESCRIPTION OF THE PREFERRED EMBODIMENTS

Figure 4:
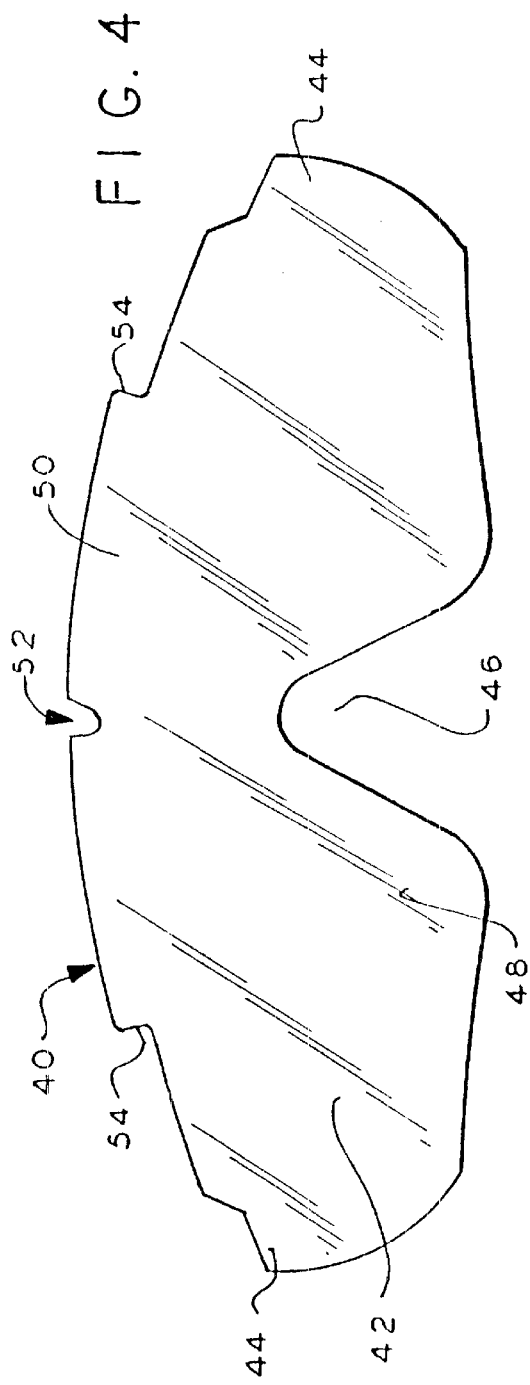
FIG. 4 is a front view of the lens member of FIG. 1.

Referring to FIG. 1, a conventional cap, such as a typical baseball-style cap 10, is illustrated in FIG. 1, the cap 10 having a head-covering portion 12, and a bill or visor 14. Bill 14 comprises an upper surface 16, edge 18 and lower surface 20.

Referring to FIGS. 2 through 4, a preferred eyeglass assembly 30 is a pair of sunglasses designed to attach to the bill 14 of the cap. The sunglasses comprise a lens member 40, a pivoting member 60 and a frame or mounting member 100, for mounting or attaching the eyeglass assembly 30 to the bill 14.

The lens member 40 comprises a single piece of lens material (FIG. 4), and, in a preferred embodiment, the lens panel 42 is curved.

The lens panel 42 is shaped to cover the eyes of the wearer, and curves, or wraps around, at the ends 44 to shield the wearer's eyes from side glare. A notch 46 for the wearer's nose is present in the lower portion 48 of the lens panel 42.

Referring to FIGS. 4 through 6, the upper portion 50 of the lens panel is designed to fit within pivoting member 60. Upper portion 50 comprises an alignment notch 52. Upper portion 50 fits into a receptacle 64 formed as a channel bordered by wall 78 and blocks 92 and terminated by end barriers 84 on pivoting member 60. Abutments 54 on lens panel 42 fit snugly into the receptacle pockets 84 of end barriers 82.

While glass could be used for the lens panel 42, a more preferable choice of material for the lens panel 42 is a plastic of the type conventionally used in sunglasses. Such plastic lenses can be made of polarized or non-polarized materials, and be of different colors, such as amber or yellow instead of a grey or blue or blueish-green color of conventional sunglass lenses. Depending upon manufacturing conditions, such lenses can include prescription lenses. Also panel 42 may be clear and function solely as an eye shield.

The lens panel 42 of the present invention is easily removable from the pivoting mechanism 60, enabling the user to replace lenses which have become worn or scratched, or if the user wants to alter lens colors or lens styles.

For a user who wears both prescription glasses and prescription sunglasses, the present invention enables that user to have a single frame for both pairs of glasses, and be able to change lenses as the user goes from inside to the outdoors, or vice-versa. For a user who needs two pairs of prescription glasses, such as one pair for distance viewing and a second pair for close-up work or reading, the present invention enables the user to change such prescription lenses easily.

Pivot member 60 receives lens member 40, and connects lens member 40 with the frame or mounting member 100 (FIG. 5). Pivot member comprises an arcuate body 62 including a lens retaining receptacle 64, and a hinge 66, the body 62 and hinge 66 connected by middle member 68.

Lens retaining receptacle 64 is formed by a curvilinear wall 78 that depends from the base 70 of body 62 and which extends for the length of body 62. The curvilinear wall 78 terminates as two curved end barriers 82 which each surround a receptacle 84 into which an edge 50 of the lens member is received and frictionally retained therein, as will be described in further detail below.

An alignment pin 88 projects from curvilinear wall 78, and extends inward (i.e. towards the wearer) as shown in FIG. 6. Alignment pin 88 is positioned near the junction of the curvilinear wall 78 and the base 70. A pair of blocks 92 depend from the underside of base 70, serving as supports to retain lens member 40 in place. The blocks 92 have a curved shape that is designed to accommodate the shape of the lens member 40. The sides of blocks 92 are generally curved, the extent of curvature varying with the design of the lens members 40. Thus, lens members 40 will fit between blocks 92 and wall 78 and will be maintained in a predetermined centered position by pockets 84 and by pin 88 fitting into notch 52.

Hinge 66 is generally circular in cross section, having as a detent feature, detent ridge 94. In some embodiments additional detent features may be employed. For example detent faces are placed on hubs 72 at each end. Hinge 66 is pivoted by means of pivot pins 74, projecting from hubs 72. As shown in FIG. 7A, hub 72 is shaped so it can retain the pivot member 60 in detent positions with respect to frame or mounting member 100. Specifically, hub 72 has next to an arcuate portion 76 two flat sides 77 that can rest flatly against mating portions of frame 100.

A detent ridge 94 having an approximately semi-cylindrical shape projects from hinge 66 of pivoting member 60. Detent ridge 94 maintains the pivot member 60 in its detent positions, and can act as a bearing as pivot member 60 is pivoted by the wearer. By using the detent features, the lens member 40 of the present invention can be pivoted into one of three positions, described, generally, as the lowered or down position (lens is down with respect to the plane of the bill 14, and is worn to cover the eyes), diagonally (an approximately 45 degree angle), whereby it partly shades the wearer's eyes, and an elevated, or raised, position (the lens is in an "up" position), where it is essentially parallel to the plane of the bill 14.

In FIG. 7B hinge 66 has rotated counterclockwise the maximum amount to bring the lens member into the down position, where the back of body 62 of the pivot member 60 hits the front of the frame 100. Spontaneous clockwise rotation of hinge 66 is prevented by quarter-round projection 132, which impedes passage of detent ridge 94. The user may next lift the lens member to the diagonal position, causing detent ridge 94 to pass by projection 132 and to fall in the corner below the projection. This position constitutes the second or diagonal detent position. Thereafter, the user may rotate the lens member to the up position, causing detent ridge 94 to fall into the groove 128 in body 102. This constitutes the third or up detent position.

Figure 9:
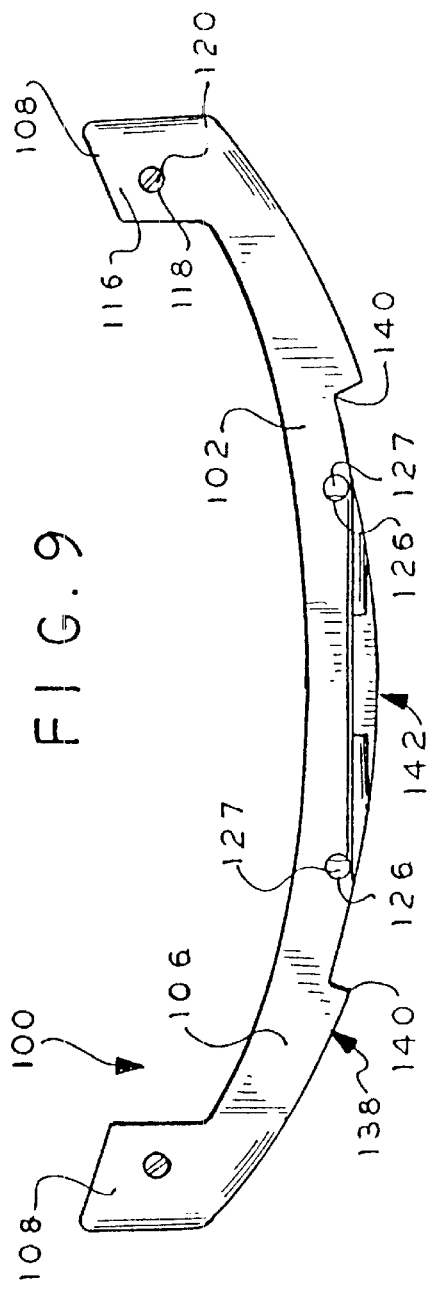
FIG. 9 is a bottom plan view of the frame of FIG. 8.

Referring to FIGS. 8 and 9, frame or mounting member 100 comprises an arcuate body 102 having a top side 104, bottom side 106 with the body terminating in two ends 108. The ends 108 are generally wider than the rest of the body 102. The ends are curved or hooked so that their upper portion 110 forms a gripper opening 112 into which the bill 14 of cap 10 is slidably received.

As shown in FIGS. 2–3, each end 108 terminates in a prong or barb 114 which is angled towards each gripper opening 112, and which prong 114 engages the upper surface 16 of bill 14 when the present device is mounted on the bill.

The bottom portion 116 (FIG. 9) of each end also includes a threaded opening 118 which receives a threaded fastener 120, such as a plastic screw, which passes from the bottom side of the frame through to the top side, and which threaded fastener 120 engages the bottom surface 18 of bill 14.

The combination of screws 120 and barbs 114 enables the present device to be retained on the bill of a cap without slipping, yet allows it to be removed at the option of the wearer. Although a slotted screw has been shown in the drawings, it is to be understood that other types of threaded fasteners, such as but not limited to, Philips, Torx, or set screws, can be substituted for it without departing from the spirit and scope of the present invention. The fastener can be manufactured from materials such as plastics, nylon, Teflon (Registered trademark of DuPont Co., Wilmington, Del.), metals or other suitable materials.

Top side 104 (FIG. 8) includes a channel 122, which is generally centrally situated, for receiving hinge 66 of pivot member 60. Each end 124 of channel 122 leads to a cavity (not shown) for receiving pivot pin 74. This cavity communicates with an opening 126 designed to receive a force-fitted pin 127 for entrapping pin 74. Each opening 126 extends through the bottom side 106 of frame 100 (FIG. 9).

Channel 122 includes previously mentioned groove 128 near its front wall 130, and the quarter-round detent feature 132 proximate its back wall 134. The height of front wall 130 is less than the height-of back wall 134, but the height of front wall extensions 136 is approximately the same height as that of back wall 134, to allow for both a smooth appearance to the eyeglass assembly 30, and allow for the smooth pivoting of the lens.

The front portion 138 of frame body 102 recesses at shoulders 140 to form a receiving region 142. Receiving region 142 receives body 62 of pivot member 60 when the lens member is lowered to either the diagonal or downward positions. In this manner, the outside of pivot member 60 provides a smooth appearance when the present device is worn with the lens in the downward position. When the lens member 40 is moved to the upward position, pivot member 60 is outside of receiving region 142, and is above top side 104 of frame.

In another embodiment of the present invention, in which a cap includes tilt-up sunglasses according to the present invention attached thereto (not shown), the bill 14 may include a pair of holes designed to fit the fasteners present in the frame.

To attach the lens member 40 to pivot member 60, the wearer holds frame 100 in one hand, and pivots pivot member 60 outwards from frame body to what would be the horizontal position. Holding lens member 40 in the other hand, the wearer inserts end 54 into pivot member 60, then aligns alignment notch 52 with the alignment pin 88, and exerts force on other end 54 of lens member until the lens member 40 becomes locked into place in pivot member 60. Pocket 84 locks the ends 54 in place in pivot member 60.

To remove the lens member 40, the wearer grasps the lens proximate the lens member's upper portion 54, flexes the lens member so that end 54 is released from the pocket 84, then pulls the lens member out of engagement with the remainder of the pivot member 60. In this manner, the lens can be replaced if it has become worn or badly scratched, or if the wearer wants to insert a different colored or shaped lens into the sunglasses of the present invention.

In an embodiment of the present invention, the pivot member 60 and the frame 100 are manufactured from plastic, but it is to be understood that other materials commonly used in the manufacture of glasses, such as, but not limited to, rubber, aluminum, titanium, monel metal and the like can be substituted therefor without departing from the spirit and scope of the present invention.

Therefore, although this invention has been described with a certain degree of particularity, it is to be understood that the present disclosure has been made only by way of illustration and that numerous changes in the details of construction and arrangement of parts may be resorted to without departing from the spirit and scope of the invention.

What is claimed is:

1. An eyeglass assembly for attachment to the bill of a cap, the eyeglass assembly comprising:
    a set of lens members having different characteristics;
    a pivot member having a lens retaining receptacle for releasably holding any one of said lens members, said lens members being interchangeable in said pivot member, said lens retaining receptacle being arranged to restrict placement of said lens members to a predetermined centered position, said pivot member including: (i) a body having a base and a wall depending from the base, and (ii) a hinge having at least one pivot pin and at least one detent feature for holding the pivot member in one or more predetermined positions; and
    a frame terminating in a pair of ends each having a curved upper portion, the ends including a gripper opening for gripping the bill of a cap.

2. The eyeglass assembly as described in claim 1 wherein said set of lens members have alternate styles or colors.

3. The eyeglass assembly as described in claim 1 wherein each of said lens members has an alignment notch.

4. The eyeglass assembly as described in claim 3 wherein said wall includes an alignment pin sized and positioned to engage said alignment notch when one of the lens member is received in the lens retaining receptacle.

5. The eyeglass assembly as described in claim 4 wherein the lens members each have an upper portion with a pair of abutments sized to be received in and laterally constrained by the lens retaining receptacle.

6. The eyeglass assembly as described in claim 4 wherein the lens retaining member further comprises a block, the block being separated from the wall by a distance sufficient to receive the lens member therebetween.

7. The eyeglass assembly as described in claim 1 wherein said lens retaining receptacle has a pair of end barriers for restricting lateral shifting of a retained one of said lens members retained in said lens retaining receptacle.

8. The eyeglass assembly as described in claim 7 wherein each of said lens members has a upper portion with a pair of abutments sized to engage and be laterally restrained by said end barriers.

9. The eyeglass assembly as described in claim 1 wherein the upper portion of said frame includes a barb for enhancing the gripping of said gripper.

10. The eyeglass assembly as described in claim 1 wherein said frame has at each end a threaded opening located at the gripper, the eyeglass assembly including a pair of fasteners threadably and adjustably mounted in said threaded openings for engaging the bill when the fasteners are urged into engagement with the bill.

11. The eyeglass assembly as described in claim 1 wherein the detent feature comprises a detent ridge attached to the hinge for holding the pivot member in one or more predetermined positions.

12. The eyeglass assembly as described in claim 11 wherein the frame has a plurality of concavities for receiving and detaining the detent ridge.

13. The eyeglass assembly as described in claim 12, wherein the alignment pin is centrally positioned on the wall, and wherein the alignment notch is centrally positioned on the lens member.

14. An eyeglass assembly for attachment to the bill of a cap, the eyeglass assembly comprising:
    (a) a lens member, comprising a lens panel having an upper portion, an alignment notch therein, the upper portion including a pair of ends,
    (b) a pivot member comprising:
        (i) a body including a base, and a curvilinear wall depending from the base, the curvilinear wall having an alignment pin connected thereto, the curvilinear wall terminating in a pair of curved ends, thereby forming a lens retaining member, the curved ends further comprising a receptacle therein for receiving the lens member;
        (ii) a hinge connected to the body and including a detent ridge, the lens member being removable and interchangeable from the pivot member; and
    (c) a frame comprising an arcuate body terminating in a pair of ends, the ends having a curved upper portion terminating in a barb, the ends including a gripper opening therein into which gripper opening the bill of a cap is receivable with the barb gripping the bill, the ends of the frame having a threaded opening in a lower portion of the body end, each threaded opening receiving a fastener therethrough, the bill being received within the gripper opening, and the fastener engaging the bill when the fastener is urged into engagement with the bill.

15. In combination, an eyeglass assembly attached to the bill of a cap, the eyeglass assembly comprising:
    (a) a lens member comprising a lens panel having an upper portion with an alignment notch therein;
    (b) a pivot member comprising:
        (i) a body including a base, and a curvilinear wall depending from the base, the curvilinear wall having an alignment pin connected thereto, the curvilinear wall terminating in air of curved ends, thereby forming a lens retaining member, the curved ends further comprising a receptacle therein for receiving the lens member;

(ii) a hinge having a detent ridge and terminating in a pair of pins; and (iii) a middle member connecting the lens retaining member with the hinge, wherein the lens member is removable from the pivot member and interchangeable; and (c) a frame comprising an arcuate body terminating in a pair of ends, the ends having a curved upper portion, terminating in a barb, the ends including a gripper opening therein receiving the bill of the cap, the barb gripping the bill; and a threaded opening in a lower portion of the body end, each threaded opening receiving a fastener therethrough, the fastener being in threaded engagement with the bill.

16. The assembly as described in claim 15 wherein the alignment pin is received in the alignment notch when the lens member is received in the lens retaining member.

17. The assembly as described in claim 16 wherein the lens member further comprises an upper portion having a pair of abutments, and wherein the abutments are received in the receptacle.

18. The assembly as described in claim 17 wherein the lens retaining member further comprises a block, the block being separated from the curvilinear wall by a distance sufficient to receive the lens member therebetween.

19. The assembly as described in claim 18 wherein the alignment pin is centrally positioned on the curvilinear wall, and wherein the alignment notch is centrally positioned on the lens member.

* * * * *